(12) United States Patent
Bulcourt et al.

(10) Patent No.: US 6,245,821 B1
(45) Date of Patent: Jun. 12, 2001

(54) ALKYL POLYGLYCOSIDES-BASED COMPOSITIONS AND USES THEREOF, AND PREPARATION OF STABLE EMULSIONS WITH IMPROVED WHITENESS

(75) Inventors: Catherine Bulcourt, Boulogne-Billancourt; Chantal Amalric, Blan; Alicia Roso, Saix; Nelly Michel, Maisons Alfort; Alain Milius, Nice, all of (FR)

(73) Assignee: Societe d'Exploitation de Produits pour les Industries Chimiques - Seppic, Paris Cedex (FR)

( * ) Notice: Subject to any disclaimer, the term of this patent is extended or adjusted under 35 U.S.C. 154(b) by 0 days.

(21) Appl. No.: 09/396,721

(22) Filed: Sep. 15, 1999

(30) Foreign Application Priority Data

Sep. 17, 1998 (FR) .................................................. 98 11612

(51) Int. Cl.[7] ................ B01F 3/08; B01F 17/56
(52) U.S. Cl. ..................... 516/72; 514/844; 514/846; 514/938; 514/975
(58) Field of Search ................ 516/72, 74; 514/844, 514/846, 938, 975; 510/470

(56) References Cited

U.S. PATENT DOCUMENTS

| | | | |
|---|---|---|---|
| 4,749,517 | * 6/1988 | Chwang et al. | 514/844 X |
| 4,889,925 | * 12/1989 | Schmid et al. | 514/844 X |
| 5,166,194 | * 11/1992 | Walker et al. | 514/975 X |
| 5,494,938 | * 2/1996 | Kawa et al. | 514/844 X |
| 5,510,100 | * 4/1996 | Picard et al. | 514/938 X |
| 5,605,651 | * 2/1997 | Balzer | 516/72 X |
| 5,670,471 | 9/1997 | Amalric et al. | 510/416 |
| 5,795,978 | 8/1998 | Ansmann et al. | 510/417 X |
| 5,817,254 | * 10/1998 | Wadle et al. | 516/72 X |
| 5,888,482 | * 3/1999 | Amalric et al. | 516/72 X |
| 5,958,431 | 9/1999 | Brancq et al. | 424/401 |

FOREIGN PATENT DOCUMENTS 9822207  5/1998  (WO) .

* cited by examiner

Primary Examiner—Richard D. Lovering
(74) Attorney, Agent, or Firm—Dennison, Scheiner, Schultz & Wakeman

(57) ABSTRACT

The present invention relates to compositions based on alkyl polyglycosides and fatty alcohols, characterized in that they comprise: *5 to 60% by weight of a mixture of alkyl polyglycosides constituted essentially of: –30 to 95% by weight of a mixture of alkyl polyglycosides of formulae (I) and (II):

$$R_1O(G_1)_{x_1} \quad (I)$$

$$R_2O(G_2)_{x_2} \quad (II)$$

in which $R_1$ and $R_2$ each represent a linear or branched aliphatic radical having 16 and 18 carbon atoms respectively, $G_1$ and $G_2$ each represent a saccharide residue, and $x_1$ and $x_2$ each represent a number between 1 and 5; –70 to 5% by weight of a mixture of alkyl polyglycosides of formulae (III) and (IV):

$$R_3O(G_3)_{x_3} \quad (III)$$

$$R_4O(G_4)_{x_4} \quad (IV)$$

in which $R_3$ and $R_4$ each represent a linear or branched aliphatic radical having 20 and 22 carbon atoms respectively, $G_3$ and $G_4$ each represent a saccharide residue, $x_3$ and $x_4$ each represent a number between 1 and 5; *95 to 40% by weight of one or more alcohols of formula R'OH, in which R' is a linear or branched aliphatic radical having 14 to 22 carbon atoms, and preferably of a mixture constituted of alcohols the alkyl part of which is identical to the alkyl part $R_1$, $R_2$, $R_3$ and $R_4$ of the above-mentioned alkyl polyglycosides.

13 Claims, No Drawings

ALKYL POLYGLYCOSIDES-BASED COMPOSITIONS AND USES THEREOF, AND PREPARATION OF STABLE EMULSIONS WITH IMPROVED WHITENESS

Alkyl polyglycosides-based compositions and uses thereof, and preparation of stable emulsions with improved whiteness.

BACKGROUND OF THE INVENTION

The present invention relates to a novel family of compositions based on alkyl polyglycosides and fatty alcohols, which are especially useful for the preparation of stable emulsions the whiteness of which is improved with respect to that obtained with compositions of the state of the art.

The invention especially finds application in the cosmetic field.

Alkyl glycosides or alkyl polyglycosides (APG's) are well-known non-ionic surfactant compounds which can be used alone or in combination with other surfactants in a wide range of industrial applications, and especially in the cosmetic field.

Alkyl polyglycosides have firstly been used as foaming agents, and in this application, those the alkyl chain of which comprises 8 to 14 carbon atoms have proved to be particularly interesting.

More recently, alkyl polyglycosides have been used as emulsifiers, and in this application, those the alkyl chain of which comprises 16 to 18 carbon atoms have proved to be particularly interesting.

The patent application WO 92/06778, in the name of the Applicant, describes, for the first time, the use of mixtures of alkyl polyglycosides and fatty alcohols as self-emulsifying agents.

The term <<self-emulsifying>> designates any agent or composition which is capable of forming a stable emulsion with an aqueous phase, practically without the provision of energy, for example by dispersion in the aqueous phase by slow mechanical agitation.

More specifically, the mixtures described in this prior art document comprise:
- 60 to 90% by weight of at least one fatty alcohol having 12 to 22 carbon atoms, and preferably 16 to 18 carbon atoms; and
- 10 to 40% by weight of an alkyl polyglycoside, the alkyl part of which is preferably identical to that of the fatty alcohol.

The self-emulsifiable compositions described in the above-mentioned application are marketed under the designation Montanov® 68 and comprise a mixture of alkyl polyglycosides the fatty chains of which comprise 16 and 18 carbon atoms, as well as a mixture of fatty alcohols of the same fatty chain length.

If such compositions are perfectly satisfactory especially as regards the stability of the emulsions that they enable obtaining, it has been observed that these emulsions were not entirely satisfactory from the point of view of their whiteness, and this constitutes a non-negligible drawback for their applications in the cosmetic field.

SUMMARY OF THE INVENTION

Under these circumstances, the aim of the present invention is to solve the technical problem consisting of providing novel compositions which enable the preparation of emulsions whose whiteness properties are significantly improved with respect to those of the emulsions obtained from compositions described in the state of the art the contents of which has been given above, without notable loss of stability.

The solution in accordance with the present invention for solving this technical problem consists of novel compositions based on alkyl polyglycosides and fatty alcohols, characterised in that they comprise:

5 to 60% by weight of a mixture of alkyl polyglycosides constituted essentially of:

30 to 95% by weight of a mixture of alkyl polyglycosides of formulae (I) and (II):

  (I)

  (II)

in which $R_1$ and $R_2$ each represent a linear or branched aliphatic radical having 16 and 18 carbon atoms respectively, $G_1$ and $G_2$ each represent a saccharide residue, and $x_1$ and $x_2$ each represent a number between 1 and 5;

70 to 5% by weight of a mixture of alkyl polyglycosides of formulae (III) and (IV):

  (III)

  (IV)

in which $R_3$ and $R_4$ each represent a linear or branched aliphatic radical having 20 and 22 carbon atoms respectively, $G_3$ and $G_4$ each represent a saccharide residue, and $x_3$ and $x_4$ each represent a number between 1 and 5;

95 to 40% by weight of one or more alcohols of formula R'OH, in which R' is a linear or branched aliphatic radical having 14 to 22 carbon atoms, and preferably of a mixture constituted of alcohols the alkyl part of which is identical to the alkyl part $R_1$, $R_2$, $R_3$ and $R_4$ of the above-mentioned alkyl polyglycosides.

Advantageously, the above-mentioned mixture of alcohols is constituted essentially of:
- 10 to 98% by weight of at least one alcohol having 16 to 18 carbon atoms;
- 90 to 2% by weight of at least one alcohol having 20 to 22 carbon atoms.

DETAILED DESCRIPTION OF THE INVENTION

Such compositions based on alkyl polyglycosides and fatty alcohols thus essentially differ from compositions of the state of the art by the fact that the necessarily comprise alkyl polyglycosides the alkyl part of which comprises 20 and 22 carbon atoms, in combination, in determined proportions, with alkyl polyglycosides the alkyl part of which comprises 16 and 18 carbon atoms.

It has been discovered, in an entirely surprising and unexpected way, that such compositions enable obtaining emulsions which possess remarkable whiteness properties which are particularly interesting for their uses in the cosmetic field without notable loss of stability.

A preferred sub-family of compositions based on alkyl polyglycosides and fatty alcohols which can be used within the context of the present invention is constituted of the compositions the above-mentioned mixture of alkyl polyglycosides of which is constituted essentially of:
- 30 to 70% by weight of a mixture of alkyl polyglycosides of formulae (I) and (II) as defined above; and
- 70 to 30% by weight of a mixture of alkyl polyglycosides of formulae (III) and (IV) as defined above.

The preferred compositions within the context of the present invention are the compositions which comprise:

5 to 40% by weight, and preferably 10 to 20% by weight, of the above-mentioned mixture of alkyl polyglycosides; and 95 to 60% by weight, and preferably 90 to 80% by weight, of one or more alcohols mentioned above.

Compositions which are particularly preferred within the context of the present invention comprise:

5 to 60% by weight, and preferably 10 to 20% by weight, of a mixture of alkyl polyglycosides constituted essentially of:

10 to 70% by weight, and preferably 10 to 45% by weight, of an alkyl polyglycoside of formula (I) as defined above, 15 to 70% by weight, and preferably 15 to 45% by weight, of an alkyl polyglycoside of formula (II) as defined above, 4 to 50% by weight, and preferably 4 to 45% by weight, of an alkyl polyglycoside of formula (III) as defined above, 2 to 25% by weight, of an alkyl polyglycoside of formula (IV) as defined above, 95 to 40% by weight, and preferably 90 to 80% by weight, of a mixture constituted of alcohols the alkyl part of which is identical to the alkyl part $R_1$, $R_2$, $R_3$ and $R_4$ of the above-mentioned alkyl polyglycosides, or as defined above.

The alkyl polyglycosides of formulae (I), (II), (III) and (IV) mentioned above can comprise, as a saccharide residue represented respectively by $G_1$, $G_2$, $G_3$ and $G_4$, a glucose or dextrose, fructose, galactose, maltose, maltotriose, lactose, cellobiose, mannose, ribose, dextran, talose, allose, xylose, levoglucosan, cellulose or starch residue.

Advantageously, $G_1$, $G_2$, $G_3$ and $G_4$ each represent a glucose residue.

Furthermore, it is to be noted that each unit of the polyoside part of the alkyl polyglycoside can be in an α or β anomeric form, and the saccharide residue can be of the furanoside or pyranoside type.

The indices $x_1$, $x_2$, $x_3$ and $x_4$ represent the average degree of polymerisation of the saccharide residue. Preferably, these indices will represent a number between 1.05 and 2.5, more preferably between 1.1 and 2.

The expression <<alkyl polyglycoside>> used within the context of the present application therefore equally designates alkyl monoosides (degree of polymerisation equal to 1) or alkyl polyglycosides (degree of polymerisation greater than 1).

The alkyl polyglycosides of formulae (I), (II), (III) and (IV) are compounds the alkyl radicals of which comprise chains of determined length. These compounds can however further contain minor proportions of compounds of the same nature the alkyl radicals of which comprise a longer and/or shorter chain, such compounds originating notably from fatty alcohols which are generally of natural or synthetic origin used as starting material for the synthesis of these alkyl polyglycosides.

The expression <<constituted essentially>> used within the context of the present application and claims for characterising the above-mentioned mixture of alkyl polyglycosides must therefore be understood as not excluding the presence, within the mixture of alkyl polyglycosides, of compounds the alkyl radicals of which have 10, 12 or 24 carbon atoms, in a maximum combined amount of 5% by weight, and preferably 1% by weight with respect to the total weight of the mixture of alkyl polyglycosides.

The compositions based on alkyl polyglycosides and fatty alcohols in accordance with the present invention can be prepared by simply mixing their constituents in the predetermined proportions sought after.

On an industrial scale, they will be prepared preferably according to one of the two routes classically used for the synthesis of alkyl polyglycosides, and for example by reaction, in an acid medium, between a fatty alcohol and a saccharide having an anomeric OH, such as glucose or dextrose.

Such synthetic routes are well known and have been described in numerous documents and in particular in the Applicant's documents recalled above.

If need be, it will be possible for this synthesis to be completed by operations of neutralisation, filtration, distillation or partial extraction of the excess fatty alcohol, or of decoloration.

The compositions based on alkyl polyglycosides and fatty alcohols in accordance with the present invention can be used, as main emulsifier, for the preparation of various emulsions.

Thus, according to a second aspect, the present application aims to cover emulsions comprising at least one aqueous phase and one oily phase and, as main emulsifier, a composition based on alkyl polyglycosides and fatty alcohols as defined above.

In general, such an emulsion will comprise 1 to 25% by weight, preferably 1 to 10% and more preferably 5% by weight of the self-emulsifying composition mentioned above.

The oily phase constituting the emulsion can be constituted by the fatty alcohol(s) constituting the emulsifying composition of the invention, without it being necessary to make use of another oil. However, more generally, an oil will be used which is selected from the following oils:

oils of plant origin, such as sweet almond oil, coconut oil, castor oil, jojoba oil, olive oil, rapeseed oil, groundnut oil, sunflower oil, wheat germ oil, maize germ oil, soya oil, cotton oil, lucerne oil, poppy oil, marrow oil, evening primrose oil, millet oil, barley oil, rye oil, safflower oil, canelle nut tree oil, passionflower oil, hazelnut oil, palm oil, shea butter, apricot stone oil, Alexandria laurel tree oil, sysymbrium oil, avocado oil, calendula oil;

modified plant oils such as the products known under INCI designations Apricot Kernel Oil PEG-6 esters and Olive Oil PEG-6 esters;

oils of natural origin, such as perhydrosqualene, squalene;

mineral oils, such as liquid paraffin, and mineral oils, notably originating from petroleum fractions, such as isoparaffins, having a boiling point between 300 and 400° C.;

synthetic oils, notably fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, ester derivatives of lanolic acid, such as isopropyl lanolate, isocetyl lanolate, triglycerides such as glycerol triheptanoate, alkylbenzoates, isoparaffins, polyalphaolefins, polyolefins, synthetic isoalkanes such as isohexadecane, isododecane, and silicone oils. Amongst the latter oils, dimethyl polysiloxanes, methylphenylpolysiloxanes, amine-modified silicones, fatty acid-modified silicones, alcohol-modified silicones, alcohol- and fatty acid-modified silicones, polyether group-modified silicones, epoxy-modified silicones, fluoro group-modified silicones, cyclic silicones, and alkyl group-modified silicones, may be more particularly cited.

Generally, the emulsions in accordance with the present invention will comprise up to 50%, and preferably between 10 and 30% by weight of oily phase as defined above.

These emulsions can be prepared by simple dispersion of a fatty phase constituted of the above-mentioned self-emulsifying composition and optionally of one or more oils such as the oils described above, in a hydrophilic phase, generally water or a hydrophilic solvent.

The dispersion can be carried out in the hot or in the cold as a function of the melting point of the self-emulsifying composition, it being necessary for all constituents to be liquid at the moment of mixing.

The emulsions thus obtained differ from those which can be obtained from emulsifying compositions of the state of the art, by the fact that they possess remarkable whiteness properties, as will be demonstrated further on.

These emulsions can further comprise an additional emulsifying agent in an amount such that the total amount of emulsifying agents within the emulsion be less than or equal to 25% by weight.

The invention will be illustrated in greater detail by the following Examples, which are given solely as an illustration.

EXAMPLE 1

Method of preparation of a composition based on alkyl polyglycosides and fatty alcohols according to the invention.

A fatty alcohol fraction constituted in weight percentage of 85.5% of $C_{16}$ and $C_{18}$ alcohols; and 14.5% of $C_{20}$ and $C_{22}$ alcohols, is introduced into a polyvalent reactor.

Glucose is also added into the reactor such that the molar ratio of the fatty alcohol and the glucose be: 6/1.

The glucose is then allowed to react with the fatty alcohol for 5 hours at a temperature of about 100° C., in the presence of an acid catalyst, under partial vacuum.

After reaction, the catalyst is neutralised by means of a base.

The resulting composition comprises:

85.7% of free $C_{16}$ and $C_{18}$ fatty alcohols,
4% of flee $C_{20}$ and $C_{22}$ fatty alcohols,
9.55% of $C_{16}$ and $C_{18}$ alkyl glycosides
0.75% of $C_{20}$ and $C_{22}$ alkyl glycosides.

EXAMPLES 2 to 5

Four other compositions based on alkyl polyglycosides and fatty alcohols in accordance with the invention are prepared in order to study notably the influence of the nature of the mixture of alkyl polyglycosides upon the properties obtained.

These compositions were prepared by following the experimental protocol described in Example 1, in selecting the appropriate fatty alcohols fraction.

The compositions of the mixtures of alkyl polyglycosides and fatty alcohols thus obtained are given in Table I below.

Comparative Examples 1 to 4

In order to demonstrate the particular properties of the compositions based on alkyl polyglycosides and fatty alcohols in accordance with the present invention, four compositions have been prepared as Comparative Examples.

The composition of Comparative Example 1 corresponds to a self-emulsifiable composition according to the teaching of document WO 92/06778, constituted of $C_{16}$ and $C_{18}$ alkyl polyglycosides.

The composition of Comparative Example 2 was prepared by following the experimental protocol described in Example 1, this composition being constituted essentially of $C_{20}$ and $C_{22}$ alkyl polyglycosides.

The compositions of the mixtures of the Comparative Examples 1 to 4 are also given in Table I below.

TABLE I

| | EXAMPLES ACCORDING TO THE INVENTION | | | | | COMPARATIVE EXAMPLES | | | |
|---|---|---|---|---|---|---|---|---|---|
| | 1 | 2 | 3 | 4 | 5 | 1 | 2 | 3 | 4 |
| C16 APG | 4.75 | 4.50 | 3.00 | 2.50 | 2.00 | 5.00 | 0 | 1.00 | 0.50 |
| C18 APG | 4.80 | 4.60 | 3.40 | 3.00 | 2.60 | 5.00 | 1.00 | 1.80 | 1.40 |
| 16–18 APG | 9.55 | 9.10 | 6.40 | 5.50 | 4.60 | 10.00 | 1.00 | 2.80 | 1.90 |
| C20 APG | 0.50 | 1.00 | 4.00 | 5.00 | 6.00 | 0 | 10.00 | 8.00 | 9.00 |
| C22 APG | 0.25 | 0.50 | 2.00 | 2.50 | 3.00 | 0 | 5.00 | 4.00 | 4.50 |
| C20–22 APG | 0.75 | 1.50 | 6.00 | 7.50 | 9.00 | 0 | 15.00 | 12.00 | 13.50 |
| C16 Alcohol | 42.75 | 40.50 | 27.00 | 22.50 | 18.00 | 45.00 | 0 | 9.00 | 4.50 |
| C18 Alcohol | 42.95 | 40.90 | 28.60 | 24.50 | 20.40 | 45.00 | 4.00 | 12.20 | 8.10 |
| C16–18 Alcohol | 85.70 | 81.40 | 55.60 | 47.00 | 38.40 | 90.00 | 4.00 | 21.20 | 12.60 |
| C20 Alcohol | 2.70 | 5.40 | 21.60 | 27.00 | 32.40 | 0 | 54.00 | 43.20 | 48.60 |
| C22 Alcohol | 1.30 | 2.60 | 10.40 | 13.00 | 15.60 | 0 | 26.00 | 20.80 | 23.40 |
| C20–22 Alcohol | 4.00 | 8.00 | 32.00 | 40.00 | 48.00 | 0 | 80.00 | 64.00 | 72.00 |

EXAMPLE 8

Method of preparation of emulsions from an emulsifying composition according to the invention or from an emulsifying composition according to a Comparative Example.

Various emulsions were prepared by means of the compositions of Examples 1 to 5 as well as of the compositions of Comparison Examples 1 to 4.

These emulsions were prepared in the following manner:

A mixture constituted of an emulsifying composition, an oily phase is brought to a temperature higher than the melting point of the alkyl polyglycosides composition, so as to obtain a liquid mixture.

The aqueous phase or a polar solvent is heated to the same temperature.

The two phases (oily and aqueous) are then homogenised by means of a Silverson apparatus for example for a period of time of 3 to 6 minutes at 4,000 rpm.

These emulsions are then cooled to ambient temperature under slow, anchor-type agitation.

Demonstration of the Whiteness Properties Obtained by the Implementation of the Compositions According to the Invention, by Comparison with the Compositions of the State of the Art In following the experimental protocol described in Example 8, various emulsions were prepared from compositions according to the invention which are described in Examples 1 to 5 and from comparison compositions which are described in Comparative Examples 1 and 4.

These emulsions possess the following compositions:
self-emulsifying compositions according to the invention or according to a Comparative Example: 5%,
fatty phase: 20%,
water: 75%.

The stability of the emulsions thus prepared is verified after ageing at 40° C.

The whiteness is measured with the aid of a MINOLTA CR 200 chromameter equipped with a CR-A33a protection tube.

The measurements are made by immersing the cone into 50 ml of emulsion.

The whiteness is described by the parameter L, variation from 0 to 100.

Three studies were made by varying the nature of the fatty phase.

Study 1: fatty phase=isononyl isononanoate
Study 2: fatty phase=sweet almond oil
Study 3: fatty phase=isododecane The results obtained are given in Table II below:
In this Table:
M signifies: month
Dph signifies: dephasing after
D signifies: days

TABLE II

| | EXAMPLES ACCORDING TO THE INVENTION | | | | | COMPARATIVE EXAMPLES | | | |
|---|---|---|---|---|---|---|---|---|---|
| | 1 | 2 | 3 | 4 | 5 | 1 | 2 | 3 | 4 |
| Study 1 | | | | | | | | | |
| Stability | >M3 | M3 | M2 | M1 | M1 | >M3 | dph d7 | dph d7 | dph d7 |
| L value | 89.6 | 89.7 | 89.5 | 90.0 | 90.2 | 87.6 | 90.6 | 90.3 | 90.4 |
| Study 2 | | | | | | | | | |
| Stability | >M3 | >M3 | >M3 | >M3 | >M3 | >M3 | dph M3 | dph M3 | dph M3 |
| L value | 87.9 | 87.9 | 88.0 | 88.0 | 88.4 | 84.3 | 88.2 | 88.5 | 88.8 |
| Study 3 | | | | | | | | | |
| Stability | >M3 | >M3 | M3 | M3 | M2 | >M3 | dph d1 | dph M1 | dph d7 |
| L value | 89.0 | 89.1 | 89.2 | 89.5 | 89.7 | 87.5 | 90.8 | 89.9 | 90.2 |

As Table II shows, the emulsions obtained from the self-emulsifying compositions of the invention possess a whiteness which is significantly superior to that of the emulsions obtained from the compositions of the state of the art (Comparative Example 1), without notable loss of stability, notably when the fatty phase is constituted of sweet almond oil.

The composition of the Comparative Example 2 leads to particularly white emulsions but the stability of which is notably lowered.

What is claimed is:

1. Composition based on alkyl polyglycosides and fatty alcohols, which comprises:

5 to 60% by weight of a mixture of alkyl polyglycosides constituted of:

30 to 95% by weight of a mixture of alkyl polyglycosides of formulae (I) and (II):

$$R_1O(G_1)_{x_1} \quad (I)$$

$$R_2O(G_2)_{x_2} \quad (II)$$

wherein $R_1$ and $R_2$ each represent a linear or branched aliphatic radical having 16 and 18 carbon atoms respectively, $G_1$ and $G_2$ each represent a saccharide residue, and $x_1$ and $x_2$ each represent a number between 1 and 5;

70 to 5% by weight of a mixture of alkyl polyglycosides of formulae (III) and (IV):

$$R_3O(G_3)_{x3} \quad (III)$$

$$R_4O(G_4)_{x4} \quad (IV)$$

wherein $R_3$ and $R_4$ each represent a linear or branched aliphatic radical having 20 and 22 carbon atoms respectively, $G_3$ and $G_4$ each represent a saccharide residue, $x_3$ and $x_4$ each represent a number between 1 and 5;

95 to 40% by weight of at least one alcohol of formula R'OH, wherein R' is a linear or branched aliphatic radical having 14 to 22 carbon atoms, or of a mixture constituted of alcohols the alkyl part of which is identical to the alkyl part $R_1$, $R_2$, $R_3$ and $R_4$ of the above-mentioned alkyl polyglycosides.

2. Composition of claim 1, wherein the above-mentioned mixture of alkyl polyglycosides comprises:

30 to 70% by weight of a mixture of alkyl polyglycosides of formulae (I) and (II) as defined in claim 1;

70 to 30% by weight of a mixture of alkyl polyglycosides of formulae (III) and (IV) as defined in claim 1.

3. Composition of claim 1 comprising:

5 to 40% by weight of the above-mentioned mixture of alkyl polyglycosides; and 95 to 60% by weight of at least one alcohol mentioned above.

4. Composition of claim 1 comprising:

10 to 20% by weight of the above-mentioned mixture of alkyl polyglycosides; and 90 to 80% by weight of at least one alcohol mentioned above.

5. Composition of claim 1, wherein the above-mentioned mixture of alcohols comprises:
- 10 to 98% by weight of at least one alcohol having 16 to 18 carbon atoms;
- 90 to 2% by weight of at least one alcohol having 20 to 22 carbon atoms.

6. Composition of claim 5 comprising:
5 to 60% by weight of a mixture of alkyl polyglycosides comprising:
- 10 to 70% by weight of an alkyl polyglycoside of formula (I),
- 15 to 70% by weight of an alkyl polyglycoside of formula (II),
- 4 to 50% by weight of an alkyl polyglycoside of formula (III),
- 2 to 25% by weight of an alkyl polyglycoside of formula (IV), 95 to 40% by weight of a mixture of alcohols the alkyl part of which is identical to the alkyl part $R_1$, $R_2$, $R_3$ and $R_4$ of the above-mentioned alkyl polyglycosides.

7. Composition of claim 5 comprising:
5 to 60% by weight of a mixture of alkyl polyglycosides comprising:
- 10 to 45% by weight of an alkyl polyglycoside of formula (I),
- 15 to 45% by weight of an alkyl polyglycoside of formula (II),
- 4 to 45% by weight of an alkyl polyglycoside of formula (III),
- 2 to 25% by weight of an alkyl polyglycoside of formula (IV), 90 to 80% by weight of a mixture of alcohols the alkyl part of which is identical to the alkyl part $R_1$, $R_2$, $R_3$ and $R_4$ of the above-mentioned alkyl polyglycosides.

8. Composition of claim 5 comprising:
10 to 20% by weight of a mixture of alkyl polyglycosides comprising:
- 10 to 70% by weight of an alkyl polyglycoside of formula (I),
- 15 to 70% by weight of an alkyl polyglycoside of formula (II),
- 4 to 50% by weight of an alkyl polyglycoside of formula (III),
- 2 to 25% by weight of an alkyl polyglycoside of formula (IV), 95 to 40% by weight of a mixture of alcohols the alkyl part of which is identical to the alkyl part $R_1$, $R_2$, $R_3$ and $R_4$ of the above-mentioned alkyl polyglycosides.

9. Composition of claim 5 comprising:
10 to 20% by weight of a mixture of alkyl polyglycosides comprising:
- 10 to 45% by weight of an alkyl polyglycoside of formula (I),
- 15 to 45% by weight of an alkyl polyglycoside of formula (II),
- 4 to 45% by weight of an alkyl polyglycoside of formula (III),
- 2 to 25% by weight of an alkyl polyglycoside of formula (IV), 90 to 80% by weight of a mixture of alcohols the alkyl part of which is identical to the alkyl part $R_1$, $R_2$, $R_3$ and $R_4$ of the above-mentioned alkyl polyglycosides.

10. Emulsion comprising at least one aqueous phase and one oily phase and, as main emulsifier, a composition based on alkyl polyglycosides and fatty alcohols as defined in claim 1.

11. Emulsion of claim 10 comprising 1 to 25% by weight of the above-mentioned emulsifying composition and up to 50% by weight, of the above-mentioned oily phase.

12. Emulsion of claim 10 comprising 1 to 10% by weight of the above-mentioned emulsifying composition and up to 50% by weight, of the above-mentioned oily phase.

13. Emulsion of claim 10 comprising an additional emulsifying agent, in an amount such that the total amount of emulsifying agents within the composition be less than or equal to 25% by weight.

* * * * *